United States Patent [19]

Ambrose et al.

[11] Patent Number: 5,082,992

[45] Date of Patent: Jan. 21, 1992

[54] INBRED CORN LINE PHP02

[75] Inventors: William B. Ambrose, Algona, Iowa; Thomas C. Kevern, Milton, Wis.

[73] Assignee: Pioneer Hi-Bred International, Inc., Des Moines, Iowa

[21] Appl. No.: 266,428

[22] Filed: Nov. 1, 1988

[51] Int. Cl.$^5$ .......................... A01H 5/00; A01H 4/00; A01H 1/00; C12N 5/04

[52] U.S. Cl. .................................. 800/200; 800/250; 800/DIG. 56; 47/58; 47/DIG. 1; 435/240.4; 435/240.49; 435/240.5

[58] Field of Search .................... 800/1, 200, 250, 230, 800/DIG. 56; 47/58, DIG. 1; 435/240.4, 240.49

[56] References Cited

U.S. PATENT DOCUMENTS 4,812,600 3/1989 Jensen et al. ............................ 800/1

OTHER PUBLICATIONS

Nowacki et al. (1972) Bull. de L'Acad. Polonaise des. Science 20 (10): pp. 695–698, Abstract relied on.
Bates et al. (1974) Dept Grain Sci Kans Londres Mexico, Cimmyt. Abstract relied on.
Sprague et al (1977), Jn/Corn & Cern Improvement, Ed. Sprague et al., American Soc. Agron. Madison WI. p. 316.
Galinat (1977) Jn/Corn & Corn Improvement, Ed. Sprague et al. Ameuon Soc. Agron, Madison WI. pp 1 & 35.
Green et al. (1982), Jn. Maize for Biological Research, Ed. Sheridan, pp. 367–372, Plant Mol. Biol. Assoc. U. Press N. Dakota.
Germplasm Resources Information Heterole, (1950) PI 181989, (1960) PI 262587.

Primary Examiner—Howard J. Locker
Assistant Examiner—Gary Benzion
Attorney, Agent, or Firm—Michael J. Roth

[57] ABSTRACT

According to the invention, there is provided an inbred corn line, designated PHP02. This invention thus relates to the plants and seeds of inbred corn line PHP02 and to methods for producing a corn plant produced by crossing the inbred line PHP02 with itself or with another corn plant. This invention further relates to hybrid corn seeds and plants produced by crossing the inbred line PHP02 with another corn line or plant and to crosses with related species.

8 Claims, No Drawings

INBRED CORN LINE PHP02

FIELD OF THE INVENTION

This invention is in the field of corn breeding, specifically relating to an inbred corn line designated PHP02.

BACKGROUND OF THE INVENTION

The goal of plant breeding is to combine in a single variety/hybrid various desirable traits of the parental lines. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produce a uniform population of hybrid plants that may be heterozygous for many gene loci. A cross of two plants each heterozygous at a number of gene loci will produce a population of hybrid plants that differ genetically and will not be uniform.

Corn plants (*Zea mays L.*) can be bred by both self-pollination and cross-pollination techniques. Corn has male flowers, located on the tassel, and female flowers, located on the ear, on the same plant. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (nonrecurrent parent), which carries the appropriate gene(s) for the trait in question. The progeny of this cross is then mated back to the superior recurrent parent (A) followed by selection in the resultant progeny for the desired trait to be transferred from the nonrecurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A single cross hybrid corn variety is the cross of two inbred lines, each of which may have one or more desirable characteristics lacked by the other or which complement the other. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

The development of a hybrid corn variety involves three steps: (1) the selection of superior plants from various germplasm pools; (2) the selfing of the superior plants for several generations to produce a series of inbred lines, which although different from each other, each breed true and are highly uniform; and (3) crossing the selected inbred lines with unrelated inbred lines to produce the hybrid progeny ($F_1$). During the inbreeding process the vigor of the lines decreases. Vigor is restored when two unrelated inbred lines are crossed to produce the hybrid progeny ($F_1$). An important consequence of the homozygosity and homogeneity of the inbred lines is that the hybrid between any two inbreds will always be the same. Once the inbreds that give the best hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop stable, high-yielding corn hybrids that are agronomically sound. The reasons for this goal are obvious: to maximize the amount of grain produced on the land used and to supply food for both animals and humans. To accomplish this goal, the corn breeder must select and develop corn plants that have the traits that result in superior inbred parental lines for producing hybrids.

SUMMARY OF THE INVENTION

According to the invention, there is provided a novel inbred corn line, designated PHP02. This invention thus relates to the seeds of inbred corn line PHP02, to the plants of inbred corn line PHP02, and to methods for producing a corn plant produced by crossing the inbred line PHP02 with itself or another corn line. This invention further relates to hybrid corn seeds and plants produced by crossing the inbred line PHP02 with another corn line or a related species.

DEFINITIONS

In the description and examples that follow, a number of terms are used herein. In order to provide a clear and consistent understanding of the specification and claims, including the scope to be given such terms, the following definitions are provided:

Predicted RM. This trait, predicted relative maturity (RM), for a hybrid is based on the harvest moisture of the grain. The relative maturity rating is based on a known set of checks and utilizes standard linear regression analyses and is referred to as the Minnesota Relative Maturity Rating System.

MN RM. This represents the Minnesota Relative Maturity Rating (MN RM) for the hybrid and is based on the harvest moisture of the grain relative to a standard set of checks of previously determined MN RM rating. Regression analysis is used to compute this rating.

Selection Index. The selection index gives a single measure of the hybrid's worth based on information for up to five traits. A corn breeder may utilize his or her own set of traits for the selection index. One of the traits that is almost always included is yield. The selection index data presented in the tables in the specification represent the mean value averaged across testing stations.

Yield (Bushels/Acre). The yield in bushels/acre is the actual yield of the grain at harvest adjusted to 15.5% moisture.

Percent Yield. The percent yield is the yield obtained for the hybrid in terms of percent of the mean for the experiments in which it was grown.

Moisture. The moisture is the actual percentage moisture of the grain at harvest presented in percent of the mean for the experiments in which the hybrid was grown.

GDU Shed. The GDU is the number of growing degree units (GDU) or heat units required for an inbred line or hybrid to reach anthesis or pollen shed from the time of planting. Growing degree units are calculated by the Barger Method, where the heat units for a 24-hour period are:

$$GDU = \frac{(Max. + Min.)}{2} - 50$$

The highest maximum used is 86° F. and the lowest minimum used is 50° F. For each hybrid it takes a certain number of GDUs to reach various stages of plant development. GDUs are a way of measuring plant maturity. The data is given in percent of the mean for the experiments in which the hybrid was grown.

Stalk Lodging. This is the percentage of plants that do not stalk lodge, i.e., stalk breakage, as measured by either natural lodging or pushing the stalks and determining the percentage of plants that break off below the ear. This is a relative rating of a hybrid to other hybrids for standability. The data are given as the percentage of the mean for the experiments in which the hybrid was grown.

Root Lodging. The root lodging is the percentage of plants that do not root lodge; i.e., those that lean from the vertical axis at an approximately 30° angle or greater would be counted as root lodged. The data is given in percentage of mean of the experiments in which the hybrid was grown.

Barren Plants. This is the number of the plants per plot that were not barren (lack ears). The data is converted to percent of the mean for the experiments in which the hybrid was grown.

Stay Green. Stay green is the measure of plant health near the time of black layer formation (physiological maturity). A high score indicates better late-season plant health. The data is given in percentage of means of the experiments in which the hybrid was grown.

Test Weight. This is the measure of the weight of the grain in pounds for a given volume (bushel) adjusted for percent moisture. The data is given in percentage of mean of the experiments in which the hybrid was grown.

Cob Score. The cob score is a rating of how well the grain is shelled off the cob and how badly the cob is broken up going through the combine. This is given as a 1 to 9 score with 9 being good. A high score indicates that the grain shells off of the cob well, and the cob does not break. The data is given in percentage of means of the experiments in which the hybrid was grown.

Grain Quality. This is a 1 to 9 rating for the general quality of the shelled grain as it is harvested based on the color of the harvested grain, any mold on the grain, and any cracked grain. High scores indicate good grain quality. The data is given in percentage of mean of the experiments in which the hybrid was grown.

Seedling Vigor. This is the visual rating (1 to 9) of the amount of vegetative growth after emergence at the seedling stage (approximately five leaves). A higher score indicates better vigor. The data is given in percentage of mean of the experiments in which the hybrid was grown.

Early Stand Count. This is a measure of the stand establishment in the spring and represents the number of plants that emerge on a per-plot basis for the hybrid. The data is given in percentage of mean of the experiments in which the hybrid was grown.

Plant Height. This is a measure of the height of the hybrid from the ground to the tip of the tassel and is measured in inches. The data is given in percentage of mean of the experiments in which the hybrid was grown.

Ear Height. The ear height is a measure from the ground to the top developed ear node attachment and is measured in inches. The data is given in percentage of means of the experiments in which the hybrid was grown.

Dropped Ears. This is a measure of the number of dropped ears per plot and represents the number of plants that did not drop ears prior to harvest. The data is given in percentage of mean of the experiments in which the hybrid was grown.

Brittle Stalks. This is a measure of the stalk breakage near the time of pollination of the hybrids, and is an indication of whether a hybrid would snap or break at the time of flowering under severe winds. Data are presented as percentage of plants that did not snap. The data is given in percentage of means of the experiments in which the hybrid was grown.

DETAILED DESCRIPTION OF THE INVENTION

Inbred corn line PHP02 is a yellow dent corn inbred that gives superior characteristics in hybrid combination and is an excellent parental line in crosses for producing first generation F1 corn hybrids. PHP02 was developed from the single cross PHG44/PHG29 by selfing and using the ear-row pedigree method of breeding. A complete description of the development PHP02 is given in Table No. 2. Both parents, PHG44 and PHG29 (PVP Certificate 8600047) are proprietary inbred lines of Pioneer Hi-Bred International, Incorporated. The initial cross between PHG44 and PHG29 was made at Johnston, Iowa and the F1 single cross was selfed at Homestead, Fla. The F2 population was grown at Algona, Iowa and 7 ears were saved out of the population. The F3 progenies were grown at Janesville, Wis. and selfing and selection were practiced to develop PHP02. Testcrosses were made to inbred testers and evaluated by the Janesville Research Station. Based on the performance of the line per se and in testcrosses PHP02 was then evaluated in hybrid combination and as a line per se extensively by Pioneer Research Station across the northern Corn Belt.

The inbred is adapted over a wide area of the northern Corn Belt and can be used advantageously in hybrids from approximately 95–114 RM based on the Minnesota Relative Maturity Rating System for harvest moisture of the grain. PHP02 is an outstanding female and over 162 replications of research testing has averaged 90 bushels per acre or 126 percent of the experimental mean. Cold test is very adequate as a female as it has averaged 90 percent (103 percent of experimental mean) over 26 reps of data. Kernal size out is also very good for PHP02 and it has approximately 41 percent of the kernals falling in the medium flat category. Although PHP02's primary use would be as a female, it is also an acceptable male with a little below average pollen shed ability. Over 12 reps of date, it has a pollen percentage of 92 percent of the mean of 1.28 grams of pollen per plant. Under extreme heat and drought stress, PHP02 may top fire and have some tassel blasting (necrosis of top leaves and tassel, respectively). It does shed for a fairly short duration and should be planted at higher densities to ensure adequate pollen in the production of hybrid seed corn if it is used as a male.

The inbred has shown uniformity and stability within the limits of environmental influence for all traits as described in the Variety Description Information. However, the line did show segregation for yellow and purple anther color with the first foundation increase. Additional ear-to-row selection for yellow anther type has fixed the inbred for yellow anther color. PHP02 has been self-pollinated and ear-rowed a sufficient number of generations with careful attention to uniformity to plant type to ensure homozygousity and phenotypic stability. The line has been increased both by hand and sibbed in isolated fields with continued observation for uniformity. Besides the initial segregation for anther color, no variant traits have been observed or are expected with PHP02.

Inbred corn line PHP02, being substantially homozygous, can be reproduced by planting seeds of the line, growing the resulting corn plants under self-pollinating or sibpollinating conditions with adequate isolation, and harvesting the resulting seed, using techniques familiar to the agricultural arts.

The data given in the Variety Description Information (Table 1) was collected primarily at Johnston, Iowa.

TABLE 1

PHP02
VARIETY DESCRIPTION INFORMATION

Type: Dent
Region Best Adapated: Most Regions

A. Maturity: Zone 0: Averaged across maturity zones
  INBRED = PHP02
  Heat Unit Shed: 1340
  Heat Unit Silk: 1360
  No. Reps: 67
  HEAT UNITS =
  $$\frac{[\text{Max. Temp. } (\leqq 86° \text{ F.}) + \text{Min. Temp } (\geqq 50° \text{ F.})]^*}{2} - 50$$

*If maximum is greater than 86 degress fahrenheit, then 86 is used and if minimum is less than 50, then 50 is used. Heat units accumulated daily and can not be less than 0.

B. Plant Characteristics:
  Plant height (to tassel tip): 203 cm
  Length of top ear innernode: 12 cm
  Number of ears per stalk: Slight two-earred tendency
  Ear height (to base of top ear): 81 cm
  Number of tillers: None
  Cytoplasm type: Normal C. Leaf:
  Color: Medium Green (WF9)
  Angle from Stalk: 30–60°
  Marginal Waves: Few (WF9)
  Number of Leaves (mature plants): 18
  Sheath Pubescence: Light (W22)
  Longitudinal Creases: Absent (OH51)
  Length (Ear node leaf): 86 cm
  Width (widest point, ear node leaf): 94 mm D. Tassel:
  Number lateral branches: 16
  Branch Angle from central spike: 30–45°
  Pollen Shed: Medium
  Peduncle Length (top leaf to basal branches): 18 cm
  Anther Color: Yellow - was segregating for purple and yellow anther color but fixed for yellow
  Glume Color: Green E. Ear (Husked Ear Data Except When Stated Otherwise):
  Length: 20 cm
  Weight: 127 gm
  Mid-point Diameter: 42 mm
  Silk color: Salmon
  Husk Extension (Harvest stage): Short (ear exposed)
  Husk Leaf: Long >15 cm
  Taper of Ear: Average Taper
  Position of Shank (dry husks): Upright
  Kernel Rows: Distinct, Straight, Number = 16
  Husk Color (fresh): Light Green
  Husk Color (dry): Buff
  Shank Length: 10 cm
  Shank (No. of internodes): 6

F. Kernel (Dried):
  Size (from ear mid-point)
  Length: 10 mm
  Width: 7 mm
  Thick: 4 mm
  Shape Grade (% rounds): 20–40% based on Parent test
  Pericarp Color: Colorless
  Aleurone Color: Homozygous yellow
  Endosperm Color: Yellow
  Endosperm Type: Normal
  Gm Wt/100 Seeds (unsized): 26 gm G. Cob:
  Diameter at mid-point: 25 mm
  Strength: Strong
  Color: Red H. Diseases:
  Northern Leaf Blight: Susceptible
  Goss' Bacteria Blight: Intermediate
  Southern Leaf Blight: Susceptible
  Head Smut: Susceptible
  Common Smut: Resistant
  Stewart's Bacterial Wilt: Susceptible
  Corn Lethal Necrosis: Susceptible
  Northern Leaf Spot: Susceptible
  Common Rust: Resistant
  Eye Spot: Intermediate

TABLE 1-continued

PHP02
VARIETY DESCRIPTION INFORMATION

| | Type: | Dent |
|---|---|---|
| | Region Best Adapated: | Most Regions |
| | Gray Leaf Spot: Susceptible | |
| | Fusarium Ear Rot: Susceptible | |
| I. | Insects: | |
| | European Corn Borer: Susceptible | |
| J. | Variety Most Closely Resembling: | |
| | Character | Inbred |
| | Maturity | PHG29 |
| | Plant Type | PHG29 |
| | Ear Type | PHG29 |
| | Kernel Type | PHG29 |
| | Usage | PHG29 |

Inbred corn line PHP02 most closely resembles PHG29 in characteristics of maturity, plant type, ear type, kernal type, and usage.

TABLE 2

BREEDING HISTORY FOR PHP02

| Season/Year | Level | Pedigree Grown | Ears Saved |
|---|---|---|---|
| Sum/1979 | | PHG44-PHG29 (cross was made) | Bulk |
| Win/1979 | F1 | PHG44/PHG29 | Bulk |
| Sum/1980 | F2 | PHG44/PHG29)X | 7 |
| Sum/1981 | F3 | PHG44/PHG29)X1 | 2 |
| Sum/1982 | F4 | PHG44/PHG29)X12 | 1 |
| Sum/1983 | F5 | PHG44/PHG29)X121 | 3 |
| Sum/1984 | F6 | PHG44/PHG29)X1211 | 10 |
| Sum/1985 | F7 | PHP02-1 | 10 |
| Sum/1986 | F8 | PHP02-1-9 | 10 |
| Win/1986 | F9 | PHP02-1-9-(1-10) | Bulk |
| Sum/1987 | F10 | PHP02-1-9-(1-10)-X | |
| Sum/1987 | F9 | PHP02-1-9-(1-10) | |

Electrophoresis Results

Isozyme Genotypes for PHP02

Isozyme data was generated for inbred corn line PHP02 according to the procedure described in Goodman, M. M. and Stuber, C. M., "Genetic identification of lines and crosses using isoenzyme electrophoresis," Proceeding of the Thirty-Fifth Annual Corn and Sorghum Industry Research Conference, Chicago, Ill. (1980).

Electrophoresis results comparing PHP02 to its parents, PHG44 and PHG29 are given in Table No. 3. These results provide additional support to the pedigree for PHP02.

TABLE 3

Electrophoresis results for PHP02 and its parents PHG44 and PHG29.

| | Alleles Present | | |
|---|---|---|---|
| Locus | PHP02 | PHG44 | PHG29 |
| Acp1 | 2 | 2 | 2 |
| Adh1 | 4 | 4 | 4 |
| Cat3 | 9 | 9 | 9 |
| Dia1 | 8 | 8 | 8 |
| Glu1 | 6 | 6 | 6 |
| Got1 | 4 | 4 | 4 |
| Got2 | 4 | 4 | 4 |
| Got3 | 4 | 4 | 4 |
| Idh1 | 4 | 4 | 4 |
| Idh2 | 6 | 6 | 6 |
| Mdh1 | 6 | 6 | 6 |
| Mdh2 | 3.5 | 3.5* | 3.5 |
| Mdh3 | 16 | 16 | 16 |
| Mdh4 | 12 | 12 | 12 |
| Mdh5 | 12 | 12 | 12 |
| Mmm | — | — | — |

TABLE 3-continued

Electrophoresis results for PHP02 and its parents PHG44 and PHG29.

| | Alleles Present | | |
|---|---|---|---|
| Locus | PHP02 | PHG44 | PHG29 |
| Pgm1 | 9 | 9 | 9 |
| Pgm2 | 4 | 4 | 4 |
| Pgd1 | 3.8 | 3.8 | 3.8 |
| Pgd2 | 5 | 5 | 5 |
| Phi1 | 4 | 4 | 4 |
| NO. PLANTS | 10 | 10 | 10 |

*PHG44 had slower migration at Mdh2 locus than 3.5 control genotype.

INDUSTRIAL APPLICABILITY

This invention also is directed to methods for producing a corn plant by crossing a first parent corn plant with a second parent corn plant wherein the first or second parent corn plant is an inbred corn plant from the line PHP02. Further, both first and second parent corn plants may be from the inbred corn line PHP02. Thus, any methods using the inbred corn line PHP02 are part of this invention: selfing, backcrosses, hybrid production, crosses to populations, etc. Any plants produced using inbred corn line PHP02 as a parent are within the scope of this invention. Advantageously, the inbred corn line is used in crosses with other corn inbreds to produce first generation ($F_1$) corn hybrid seeds and plants with superior characteristics.

As used herein, the terms "plant and plant parts" include plant cells, plant protoplasts, plant cell tissue culture from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Tissue culture of corn is described in European Patent Application, publication 160,390, incorporated herein by reference. Corn tissue culture procedures are also described in Green and Rhodes, "Plant Regeneration in Tissue Culture of Maize," Maize for Biological Research (Plant Molecular Biology Association, Charlottsville, Va. 1982, at 367–372. Thus, another aspect of this invention is to provide for cells which upon growth and differentiation produce the inbred line PHP02.

The utility of inbred line PHP02 also extends to crosses with other species. Commonly, suitable species will be of the family Graminaceae, and especially of the genera *Zea, Tripsacum, Coix, Schlerachne, Polytoca, Chinonachne,* and *Trilobachne,* of the tribe *Maydeae.* Of these, *Zea* and *Tripsacum,* are most preferred. Potentially suitable for crosses with PHP02 may be the various varieties of grain sorghum, *Sorghum bicolor* (L.) Moench.

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch from the wet-milling industry and corn flour from the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of inbred corn line PHP02, the plant produced from the inbred seed, the hybrid corn plant produced from the crossing of the inbred, hybrid seed, and various parts of the hybrid corn plant can be utilized for human food, livestock feed, and as a raw material in industry.

EXAMPLE

Hybrid Performance of PHP02

In the examples that follow, the key traits and characteristics of inbred corn line PHP02 are given for some of its hybrid combinations.

The data in Table No. 4 gives a comparison of PHP02 to PHG29 crossed to the same tester lines and the hybrids evaluated in the same experiments at the same locations. Both inbreds were crossed to the same seven lines and evaluated in the Eastern, Northern, Central, and Western Regions and the data presented is the overall summary and has 279 replications of data averaged over testers and locations for yield. PHP02 is similar genetically to PHG29 but does show some significant advantages. Its hybrids tend to have a little higher yield, are earlier to flower, and are a little better agronomically for stalk lodging resistance and staygreen characteristics. PHP02 hybrids do tend to have lower test weight and a little poorer grain quality than PHG29 crosses. Other attributes tend to be very similar. Drought tolerance of PHP02 hybrids have tended to be a little poorer than PHG29 crosses based on research testing. PHP02 crosses can be susceptible to ear molds and its use in areas of extreme ear mold pressure should be limited. However, the overall performance of the line in hybrid combination as well as the outstanding female parental and acceptable male parental characteristics make PHP02 a very important inbred for producing commercial single cross hybrids.

TABLE 4

Average inbred by tester performance comparing PHP02 to PHG29 crossed to the same inbred testers and grown in the same experiments. All values are expressed as percent of the experiment mean except Predicted RM, Selection Index, and Yield (Bu./Ac.).

| HYBRID | PREDICTED RM | SELECTION INDEX | YIELD (BU./AC.) | PERCENT YIELD | MOISTURE | GDU SHED | STALK LODGING |
|---|---|---|---|---|---|---|---|
| No. of Reps | 281 | 279 | 279 | 279 | 281 | 60 | 269 |
| PHG29 Crosses | 108 | 100 | 144 | 101 | 101 | 100 | 98 |
| PHP02 Crosses | 108 | 104 | 147 | 103 | 101 | 98 | 103 |
| Difference | 0 | 4 | 3 | 2 | 0 | 2 | 5 |

| HYBRID | ROOT LODGING | BARREN PLANTS | STAY GREEN | TEST WEIGHT | COB SCORE | GRAIN QUALITY | SEEDLING VIGOR | EARLY STAND COUNT |
|---|---|---|---|---|---|---|---|---|
| No. of Reps | 96 | 27 | 171 | 281 | 30 | 180 | 107 | 188 |
| PHG29 Crosses | 103 | 100 | 92 | 100 | 93 | 100 | 102 | 102 |
| PHP02 Crosses | 100 | 100 | 101 | 98 | 87 | 95 | 108 | 102 |
| Difference | 3 | 0 | 9 | 2 | 6 | 5 | 6 | 0 |

| HYBRID | PLANT HEIGHT | EAR HEIGHT | DROPPED EARS | BRITTLE STALKS |
|---|---|---|---|---|
| No. of Reps | 145 | 145 | 247 | 44 |
| PHG29 Crosses | 100 | 99 | 100 | 100 |
| PHP02 Crosses | 101 | 98 | 99 | 99 |
| Difference | 1 | 1 | 1 | 1 |

Deposits

Applicants have made available to the public without restriction a deposit of at least 2500 seeds of inbred PHP02 with the American Type Culture Collection (ATCC), Rockville, Md. 20852 USA, ATCC Deposit No. 75077. The seeds deposited with the ATCC are taken from the same deposit maintained by Pioneer Hi-Bred International Inc., 700 Capital Square, 400 Locust Street, Des Moines, Iowa 50309 since prior to the filing date of this application. The deposit will be maintained in the ATCC depository, which is a public depository, for a period of 30 years, or 5 years after the most recent request, or for the effective life of the patent, whichever is longer, and will be replaced if it becomes nonviable during that period.

What is claimed is:

1. Inbred corn seed designated PHP02 having ATCC accession No.

2. A corn plant produced by the seed of claim 1.

3. Tissue culture of the plant of claim 2.

4. Tissue culture according to claim 3 comprising regenerable cells of a plant part selected from meristematic tissue, anthers, leaves, embryos, protoplasts, and pollen.

5. A corn plant regenerated from regenerable cells of a tissue culture according to claim 4.

6. An inbred corn plant having all the physiological and morphological characteristics of the seed of claim 1.

7. A method to produce a novel hybrid corn seed comprising the steps of:
   a) planting in pollinating proximity seeds of corn inbred lines PHP02 and another inbred line;
   b) cultivating corn plants resulting from said planting until the time the plants bear flowers;
   c) emasculating the flowers of the plants of either inbred line;
   d) allowing natural cross pollinating to occur between said inbred lines; and
   e) harvesting seed produced on said emasculated plants of the inbred line.

8. An $F_1$ hybrid corn plant and seed thereof produced by crossing an inbred corn plant according to claim 2 with another, different corn plant.

* * * * *

UNITED STATES PATENT AND TRADEMARK OFFICE
CERTIFICATE OF CORRECTION

PATENT NO. : 5,082,992

DATED : January 21, 1992

INVENTOR(S) : William B. Ambrose, et al.

It is certified that error appears in the above-identified patent and that said Letters Patent is hereby corrected as shown below:

At Column 5, Line 19, please rewrite "Station" as --Stations--.

At Column 5, Line 36, please rewrite "of" as --to--.

At Column 7, Line 29, after Line Sum/1984, please rewrite "PHG44/PHG29}X1211 as --PHG44/PHG29)X1211--.

At Column 8, Line 43, please rewrite "Charlottsville" as --Charlottesville--.

At Column 10, Line 42, following "No." please insert --75077--.

Signed and Sealed this

Sixth Day of July, 1993

Attest:

MICHAEL K. KIRK

*Attesting Officer*

*Acting Commissioner of Patents and Trademarks*